(12) United States Patent
Theron et al.

(10) Patent No.: US 8,153,696 B2
(45) Date of Patent: Apr. 10, 2012

(54) MEDICINAL PREPARATION PARTICULARLY FOR THE TREATMENT OF SLIPPED DISCS HERNIAS

(75) Inventors: Jacques Theron, Fleury sur One (FR); Marc d'Aboville, Le Havre (FR); Christine Marie Joseph D'Aboville, legal representative, Le Havre (FR); Soline Alix Marie D'Aboville, legal representative, Paris (FR); Côme Philippe Guy D'Aboville, legal representative, Paris (FR); Quentin Bruno Pierre D'Aboville, legal representative, Le Havre (FR); Grégoire Michel Séverin D'Aboville, legal representative, Le Havre (FR)

(73) Assignee: Jaques Theron, Fleury Sure Orne (FR)

( * ) Notice: Subject to any disclaimer, the term of this patent is extended or adjusted under 35 U.S.C. 154(b) by 0 days.

(21) Appl. No.: 12/870,258

(22) Filed: Aug. 27, 2010

(65) Prior Publication Data
US 2010/0329991 A1    Dec. 30, 2010

Related U.S. Application Data

(62) Division of application No. 10/513,592, filed as application No. PCT/FR03/01412 on May 7, 2003, now abandoned.

(30) Foreign Application Priority Data

May 7, 2002    (FR) ...................................... 02 05819

(51) Int. Cl.
   *A61K 47/00*    (2006.01)
   *A61K 31/28*    (2006.01)

(52) U.S. Cl. .......................... 514/781; 514/492; 514/772
(58) Field of Classification Search ................... 514/781, 514/772, 492
   See application file for complete search history.

(56) References Cited

U.S. PATENT DOCUMENTS

| 2,162,028 | A |   | 6/1939  | Muskat et al. |         |
|-----------|---|---|---------|---------------|---------|
| 2,903,396 | A | * | 9/1959  | Saunders et al. | 424/9.4 |
| 5,177,056 | A |   | 1/1993  | Hilti et al.  |         |
| 5,177,066 | A |   | 1/1993  | Shimohiro et al. |      |
| 5,830,178 | A |   | 11/1998 | Jones et al.  |         |
| 6,015,541 | A |   | 1/2000  | Greff et al.  |         |

(Continued)

FOREIGN PATENT DOCUMENTS

WO    0071064 A1    11/2000

(Continued)

OTHER PUBLICATIONS

Riquelme et al., Chemonucleolysis of lumbar disc herniation with ethanol, J Neuroradiol. Dec. 2001;28(4):219-29.*

(Continued)

*Primary Examiner* — Sreeni Padmanabhan
*Assistant Examiner* — Gigi Huang
(74) *Attorney, Agent, or Firm* — Browdy and Niemark, PLLC

(57) ABSTRACT

The invention concerns a product consisting in an injection medicinal formulations comprising at least one compound to provide a viscous formulation, ethanol and at least one compound making said formulation opaque to X rays so as to control its delivery and its action. Said formulation is in particular useful for treating herniated invertebral discs but also in intervention having demonstrated the efficacy of pure ethanol: treatment of hepatocellular tumours or osteoid osteomas, renal cysts and arterial-veinous angiomas.

14 Claims, 1 Drawing Sheet

U.S. PATENT DOCUMENTS

| | | | |
|---|---|---|---|
| 6,150,022 | A | 11/2000 | Coulter et al. |
| 6,476,070 | B2 * | 11/2002 | Krall et al. ............... 514/527 |
| 2002/0115904 | A1 * | 8/2002 | Ren ............................. 600/12 |

FOREIGN PATENT DOCUMENTS

WO    0071170 A1    11/2000

OTHER PUBLICATIONS

Temenoff et al., Injectable biodegradable materials for orthopedic tissue engineering, Biomaterials, vol. 21, Issue 23, Dec. 1, 2000, pp. 2405-2412.*

Scott et al., Myelography with Pantopaque and a New Technic for Its Removal, 1944, Radiology, 43, Excerpt printed from http://radiology.rsna.org/content/43/3/241.extract, 2 pages.*

Konya et al., A New Transcatheter Method for Renal Ablation: Pure Ethiodized Oil Is an Efficient Ablative Agent, Nov. 2005, printed from http://rsna2005.rsna.org/rsna2005/v2005/conference/event_display.cfm?id=66601&em_id=4411303, 3 pages.*

Center of Environmental Health and Safety, generated Dec. 10, 2007 for pages archived Apr. 6, 2001, http://web.archive.org/web/20010406062226/http://www.cehs.siu.edu/Chemical/ethanol.htm, 3 pages.

Gennaro, Remington's Pharmaceutical Sciences, 1990, Mac Publishing Company, 18th edition, 3 pages.

Remington's Pharmaceutical Sciences, Pharmaceutical Solvents-Alcohol, 1990, Philadelphia College of Pharmacy and Science, 18th Edition, 1314-1315.

Mackevi ien et al., Solubility of cellulose acetates in magnesium perchlorate solutions, Jul. 1984, Journal of Polymer Science:Polymer Letters Edition, vol. 22 Issue 7, pp. 419-421.

* cited by examiner

MEDICINAL PREPARATION PARTICULARLY FOR THE TREATMENT OF SLIPPED DISCS HERNIAS

CROSS-REFERENCE TO RELATED APPLICATIONS

The present application is a division of application Ser. No. 10/513,592, filed Nov. 30, 2005, now abandoned which is a 371 national stage application of PCT/FR03/01412, filed May 7, 2003. The entire content of both applications are incorporated herein by reference.

The invention concerns a viscous injectable medicinal preparation containing ethanol and a compound opaque to X-rays.

It is more particularly but not exclusively applicable to the treatment of discal hernias as well as to interventional procedures where pure ethanol has been found to be effective: treatment of hepato-cellular tumours or osteoid osteomas, kidney cysts and arteriovenous angiomas.

Discal hernias are the main causes of back pains and sciaticas. They are usually related to multiple ergonomic and anatomic factors such as poor posture, abdominal and paraspinal muscle weakness, etc.

Traditional and surgical therapies are the treatment of choice in most cases. However, for certain patients with well-defined clinical and radiological criteria a percutaneous treatment can be offered.

The efficacy of percutaneous treatment for lumbar discal hernias by injection of an enzyme, chymopapain (nucleolysis: enzymatic alteration of an intervertebral disc), is well established. Nevertheless, patients with a history of allergy or those have already received nucleolysis treatment can not take advantage of this procedure.

With regard to the necrosing effect of ethanol on biological tissues absolute alcohol (anhydrous ethanol) has been used as an effective therapeutic agent in many interventional procedures such as sclerosis of the ganglia and nerves; ablation of liver tumours and kidney tumours; preoperative treatment for vertebral tumours; arteriovenous, peripheral, visceral and brain malformations, etc.

One team recently considered the use of these therapeutic properties in the treatment of back disorders. They treated lumbar discal hernias with intradiscal injections of absolute alcohol with very promising results. This percutaneous procedure has a number of advantages:
- no allergic complication,
- no local septic complication,
- less post-treatment pain,
- no shrinkage of the interdiscal space,
- no inflammatory complication,
- a shorter clinical recovery time.

Nonetheless, ethanol, because of its properties, can diffuse at a distance from its target and cause necrosis of healthy cells. This is why the team using pure ethanol contraindicated its use for discal hernias with epidural leakage as revealed by discography as well as in cases of cervical discal hernias.

Moreover, the use of alcohol in the treatment of hepato-cellular tumours can cause thrombosis of the portal vein by diffusion of the product into the venous system.

One of the applicant's objectives is to avoid the side effects of ethanol in this disorder, in other words necrosis of healthy tissues which occurs as a result of diffusion at a distance from the target as well as to reinforce effectiveness.

To this end, the applicant has tested several thickeners and is proposing an injectable medicinal preparation which comprises at least one compound used to make the preparation viscous, ethanol and at least one compound making said preparation opaque to X-rays in order to manage its administration and action.

Advantageously, viscosity limits diffusion of the preparation to a specific area and reinforces its therapeutic effect.

This preparation thus has the dual advantage of offering an active principle with limited diffusion and a marker to be able to better monitor injection as the therapist performs the procedure and, most importantly, for post-treatment monitoring of the exact location of the injected product with the aid of a scanner.

The compounds used to make the preparation opaque to X-rays can be inert compounds such as tungsten oxide or tantalum oxide.

These compounds can be added for example in powder form either at the end of the preparation manufacturing process or immediately prior to injection.

Ethylcellulose was selected as the compound (excipient) used to achieve the required viscosity. This choice is based on several criteria:
- its hydrophilic nature, given the fact that the preparation is for injection,
- its thickening capacity which has to be sufficient, even when present in small amounts, to increase the mixture's viscosity,
- cellulose derivatives are water-soluble in vitro and therefore circumvent the need for surgical resection of the treated area,
- it is in the form of a powder and not a liquid in order not to dilute the ethanol,
- a certain degree of solubility in ethanol so as to obtain a homogeneous preparation,
- systemic and/or local toxic effects reduced to a minimum, and preferably non-existent, in order not to compromise tolerance to the preparation.

Consequently, the preparation according to the invention fulfils the required criteria which are safety of use in all phases of the process and the ability to produce stable and selective sclerosis.

One mode of implementation of the invention, given as a non-limiting, example, will be described hereinafter:

CHOICE OF EXCIPIENTS USED IN THE PREPARATION

Figure 1:
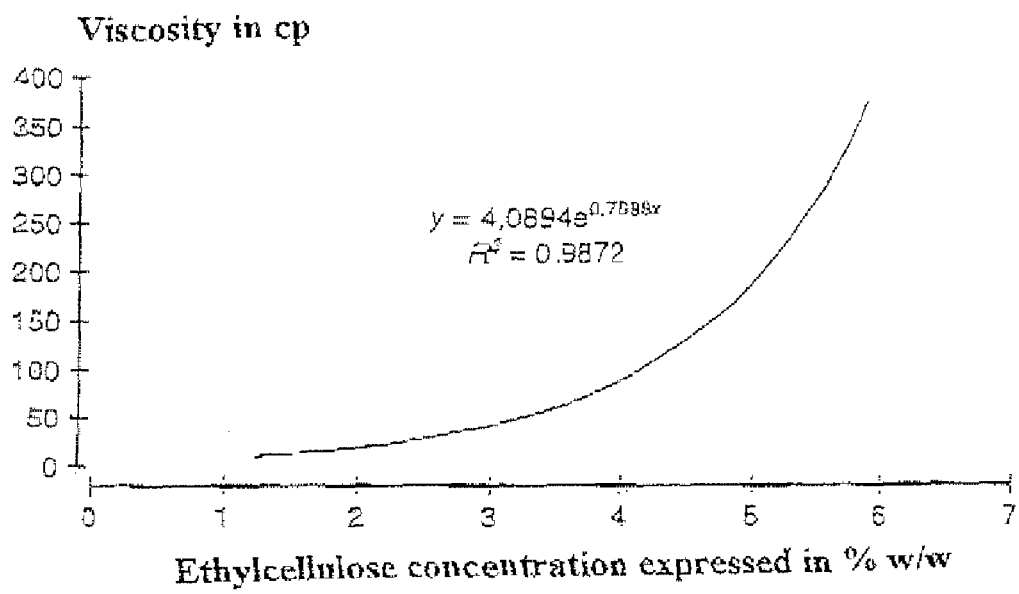
FIG. 1 represents measurement of viscosity expressed in pharmaceutical units as a function of concentration given as the percentage of ethylcellulose weight with respect to total weight.

Six products registered in the European Pharmacopoeia $3^{rd}$ edition (1999) and fulfilling the above-mentioned criteria were chosen for evaluation as an excipient (Table I). Each of these was tested for solubility in hot/cold ethanol. In addition, the physico-chemical compatibility of substances in contact with each other (by visual evaluation) and the approximate viscosity of the mixture were also examined.

TABLE I

Products tested for gel manufacture

| Products | Commercial references | Suppliers |
| --- | --- | --- |
| Hydroxycellulose | Klucel MF EP ® | Aldrich |
|  | Klucel HF EP ® |  |
| Ethylcellulose | Aqualon 100 NF ® | Hercules |
| Polysorbate | Montanox 80 ® | Seppic |
| Colloidal Silica | Aérosil R972 ® | Degussa France |
|  | Aérosil R200 ® |  |
| Carboxypolymethylene | Carbopol 940 ® | Gattefosse |
|  | Carbopol 934 ® |  |
| Polyethyleneglycol | Lutrol E4000 ® | BASF France |
|  | Lutrol E6000 ® |  |

The results of various tests are summarized in Table II. All the products tested were soluble in hot ethanol. Only ethylcellulose was also more or less soluble in cold ethanol. Moreover, the physico-chemical compatibility of the mixture (absence of precipitation) was good and viscosity was satisfactory. This is why ethylcellulose was considered to be the most suitable product.

TABLE II

Characteristics of products tested

| Products | Solubility in ethanol | | Visual examination |
| --- | --- | --- | --- |
|  | Cold | Hot |  |
| Hydroxypropylcellulose | − | + | After cooling, non- |
|  | − | + | homogeneous |
| Ethylcellulose | ± | + | Clear gel |
| Polysorbate | − | + | Very low viscosity |
| Colloidal Silica | − | + | Only becomes viscous a |
|  | − | + | few days later |
| Carboxypolymethylene | − | + | Precipitates after |
|  | − | + | neutralisation |
| Polyethyleneglycol | − | + | Precipitates on cooling |
|  | − | + |  |

Manufacture of the Preparation

Several preparations at different ethylcellulose concentrations were made up by dissolving 0.15, 0.45 and 0.75 g in 15 mL of ethanol with a purity of 70 to 99% by volume and preferably 95% (d=0.8), that is 1.22, 3.61 and 5.88% by weight of the preparation's total weight.

The preparation with the highest ethylcellulose concentration was chosen. A loss of 2.5% on distribution into bottles was observed, that is proportions of 205 mL of 95° alcohol (% volume) and 10.25 g of ethylcellulose per forty bottles.*

More generally, ethylcellulose is used at a concentration ranging from 0.5 to 15%, preferably 5.88%, by weight of the preparation's total weight.

In accordance with Good Manufacturing Practice (1998), the preparation was manufactured in three stages: gel preparation, aseptic distribution and sterilisation of the product in the final packaging. To start with, the excipient (ethylcellulose) was mixed by magnetic stirring with hot ethanol in a sterile ground-glass neck flask and refluxed until completely dissolved. The mixture was stirred and refluxed for 15 minutes then stirred until it cooled down completely in order to allow recondensation of the alcohol in the flask. It was then packaged under a horizontal laminar flux hood into 5 mL sterile bottles (bioblock 42065). Finally, in accordance with European Pharmacopoeia recommendations, the bottles were sterilised in a autoclave using saturated vapour at 121° C. for 20 minutes.

The final step in the manufacturing process of the preparation is the addition of a powdered opacifying compound such as tantalum oxide or tungsten oxide in varying proportions so as to obtain good opacity. This addition can take place either at the end of the manufacturing process prior to packaging or just before carrying out the injection.

As these compounds are inert and used in very small amounts, they do not significantly alter the results of the tests described below and carried out on the preparation prior to their addition.

Tested Carried Out

The conformity of the preparation was verified by means of a sterility test and chemical and physico-chemical tests.

In accordance with European Pharmacopoeia recommendations, the possible presence of any contaminants was investigated by culturing 4 mL of the preparation in 250 mL of tryticase-soya broth for aerobic germs, thioglycate for anaerobic germs and Sabouraud for yeasts. The results of the sterility test confirmed the absence of any contaminants in the preparation.

Alcohol content was determined after dilution of a sample and incorporation of the internal standard, propanol-1, by gas chromatography with detection by flame ionisation. Separation was by means of a Porapak Q column (80-100 mesh, length 3 m) with nitrogen as the carrier gas (1.2 bar) on a Delsi DN200 apparatus.

The alcohol assay gave a value of 802 g.$L^{-1}$.

The specific assay for the viscosity additive was not performed but the concentration was estimated by means of the dry residues method, a process which consists in evaporating ethanol in a tank whose temperature was maintained at 110° C. until the sample reached constant weight.

The dry residues method allowed a correlation to be made between the theoretical ethylcellulose concentration and the experimentally measured concentration, that is 5.88% by weight of the sample's total weight.

Figure 2:
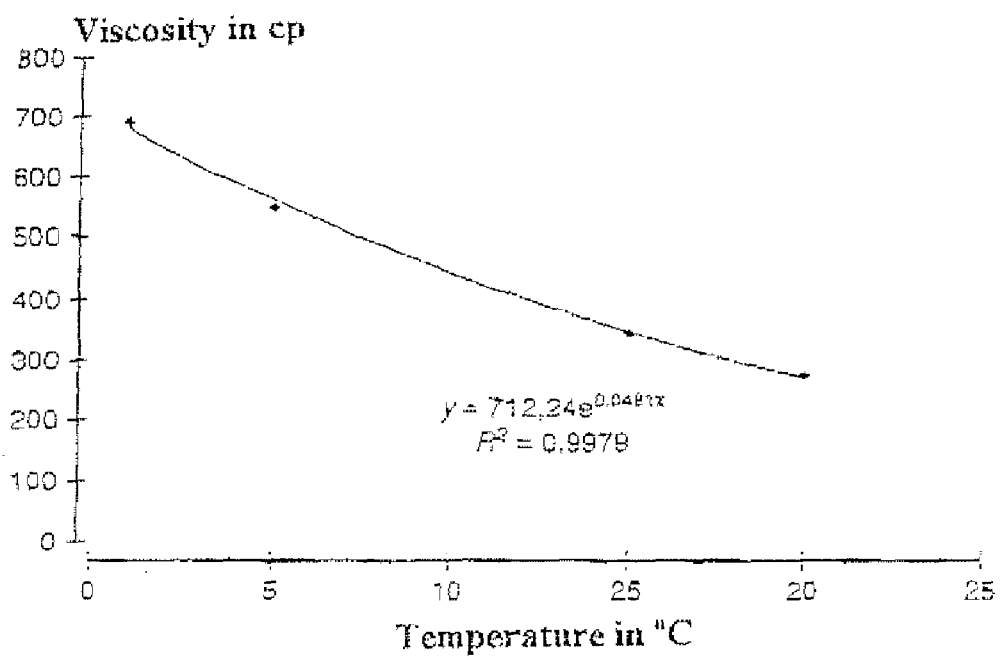
FIG. 2 represents measurement of viscosity expressed in pharmaceutical units as a function of temperature given in degrees Celsius.

The viscosity of the preparation was measured by means of a Baumé capillary viscosimeter (Prolabo). Several series of measurements were performed at different temperatures and different concentrations of the thickener. The viscosity measurements showed that, at constant temperature, the preparation increased exponentially as a function of ethylcellulose content (FIG. 1). However, it decreased, also exponentially, when the temperature increased (FIG. 2).

Finally, the physico-chemical stability study was carried out by means of analysis as a function of time of the changes in the parameters defining the preparation, on other words viscosity, ethanol content and viscosity agent. The measurements were repeated on day 1 (D1), day eight (D8), day fifteen (D15) and day thirty (D30).

The results are given in Table M. The coefficients of variation, below 3%, prove that the mixture is stable up to D30, which will allow an expiry date for the preparation to be determined.

TABLE III

Physico-chemical parameters as a function of time

| Date | $C_{ethanol}$ (g·L$^{-1}$) | $V_{éch}$ (mL) | $W_{ech}$ (g) | $D_{ech}$ (g·mL$^{-1}$) | Dry residue DR(g) | $DR/W_{ech}$ ratio (%) | Viscosity (cp)* |
|---|---|---|---|---|---|---|---|
| D1 | 784 | 2 | 1.650 | 0.825 | 0.101 | 6.10 | 320 |
| D8 | 821 | 2 | 1.720 | 0.850 | 0.103 | 5.97 | 339.5 |
| D15 | 783 | 2 | 1.610 | 0.800 | 0.097 | 6.00 | — |
| D30 | 820 | 2 | 1.670 | 0.830 | 0.099 | 5.92 | 332 |
| Mean | 802 | — | 1.663 | 0.826 | 0.100 | 5.998 | 330.5 |
| Standard deviation | 21.370 | — | 0.046 | 0.021 | 0.002 | 0.076 | 9.836 |
| Coefficient of variation | 2.665 | — | 2.751 | 2.489 | 2.458 | 1.265 | 2.976 |

*cp: pharmaceutical unit

Injection of the preparation into the lumbar disc led to decreased intra-discal pressure and, therefore, to reduced back pain caused by discal hernias.

What is claimed is:

1. A method for the treatment of discal hernias comprising a step of administering, to a patient in need thereof, a viscous non-toxic preparation comprising:
   (1) ethanol,
   (2) ethyl cellulose at a concentration ranging from 0.5% to 15% by weight of the total weight of the preparation, and
   (3) a compound to make the said preparation opaque to X-rays selected from the group consisting from tantalum and tungsten oxides,
   wherein ethanol and ethyl cellulose form a homogenous mixture.

2. The method according to claim 1, wherein ethyl cellulose is at a concentration ranging from 1.22% to 5.88% by weight of the total weight of the preparation.

3. The method according to claim 1, wherein the said compound making the said preparation opaque to X-rays consists of a tantalum oxide.

4. The method according to claim 1, wherein the said compound making the said preparation opaque to X-rays consists of tungsten oxide.

5. The method according to claim 1, wherein ethanol has a purity ranging from 70% to 99% (v/v).

6. The method according to claim 5, wherein ethanol has a purity of 95% (v/v).

7. The method according to claim 1, wherein the said viscous non-toxic preparation is administered by injection.

8. The method according to claim 1, wherein the said viscous non-toxic preparation is administered by intradiscal injection, and the quantity of said viscous non-toxic preparation injected is an amount sufficient to cause a decreased intra-discal pressure.

9. The method according to claim 2, wherein said compound making the preparation opaque to X-rays is a tantalum oxide.

10. The method according to claim 2, wherein the compound making the preparation opaque to X-rays is tungsten oxide.

11. The method according to claim 2, wherein the ethanol has a purity ranging from 70% to 99% (v/v).

12. The method according to claim 11, wherein the ethanol purity is 95% (v/v).

13. The method according to claim 2, wherein the viscous non-toxic preparation is administered by injection.

14. The method according to claim 2, wherein the said viscous non-toxic preparation is administered by intradiscal injection, and the quantity of said viscous non-toxic preparation injected is an amount sufficient to cause a decreased intra-discal pressure.

* * * * *